(12) United States Patent
Vanden Berghe

(10) Patent No.: US 7,968,528 B2
(45) Date of Patent: Jun. 28, 2011

(54) CHOLINE-SILICIC ACID COMPLEX WITH OSMOLYTES AND DIVALENT TRACE ELEMENTS

(75) Inventor: Dirk André R. Vanden Berghe, Laarne (BE)

(73) Assignee: Bio Minerals N.V., Destelbergen (BE)

( * ) Notice: Subject to any disclaimer, the term of this patent is extended or adjusted under 35 U.S.C. 154(b) by 926 days.

(21) Appl. No.: 10/508,168

(22) PCT Filed: Mar. 20, 2003

(86) PCT No.: PCT/EP03/03175
§ 371 (c)(1),
(2), (4) Date: Apr. 7, 2005

(87) PCT Pub. No.: WO03/077657
PCT Pub. Date: Sep. 25, 2003

(65) Prior Publication Data
US 2006/0165815 A1    Jul. 27, 2006

(30) Foreign Application Priority Data
Mar. 20, 2002 (EP) ................................. 02076099

(51) Int. Cl.
*A01N 55/00* (2006.01)
*A01N 59/06* (2006.01)
*A61K 31/695* (2006.01)
*A61K 33/10* (2006.01)
(52) U.S. Cl. .................................. 514/63; 424/687
(58) Field of Classification Search ............. 514/63; 424/687
See application file for complete search history.

(56) References Cited

U.S. PATENT DOCUMENTS

| 4,466,958 A | 8/1984 | Morrison |
| 5,183,061 A * | 2/1993 | Wiegand et al. ............. 128/897 |
| 5,840,881 A * | 11/1998 | Uda et al. ...................... 536/46 |
| 6,335,457 B1 * | 1/2002 | Seguin et al. ................ 556/413 |
| 2003/0049325 A1 * | 3/2003 | Suwelack et al. ............ 424/520 |

FOREIGN PATENT DOCUMENTS

| DE | 43 22 939 A1 | 1/1995 |
| EP | 0 158 120 A1 | 10/1985 |
| EP | 0 573 876 A2 | 12/1993 |
| EP | 1110909 A1 * | 6/2001 |
| WO | WO 95/21124 | 8/1995 |
| WO | WO 96/23413 | 8/1996 |

OTHER PUBLICATIONS

Good et al. Biochemistry, (1966) vol. 5, No. 2, pp. 467-477.*
Leifer et al. Journal of American Chemical Society, 1957. vol. 79, pp. 5098-5101.*
Subcommittee on Poultry Nutrition. Nutrients Requirement of Poultry, Ninth Edition (1994),pp. 1-2.*

* cited by examiner

*Primary Examiner* — Sreeni Padmanabhan
*Assistant Examiner* — Samira Jean-Louis
(74) *Attorney, Agent, or Firm* — Bozicevic, Field & Francis LLP; Bret E. Field; Rudy Ng

(57) ABSTRACT

The invention relates to a biological preparation comprising orthosilicic and silicic acid, a primary ("constant/first") osmolyt choline and a weak alkalinizing agent without free hydroxyl groups and to a method for preparing the preparation, comprising: i) hydrolysing a silicon comprising choline solution thereby forming a choline stabilized orthosilicic acid and oligomers solution; ii) alkalizing the choline orthosilicic acid and oligomers solution by adding a weak alkalizing agent without hydroxyl groups; and iii) optionally adding a divalent trace element and/or secondary osmolyte, to biological preparation obtainable and its uses.

10 Claims, No Drawings

CHOLINE-SILICIC ACID COMPLEX WITH OSMOLYTES AND DIVALENT TRACE ELEMENTS

This patent application describes the use and preparation of special choline-(ortho)silicic acid complexes for plants, animals and humans using $Ca^{2+}$ and/or osmolytes. Choline inhibits the gelification of highly concentrated orthosilicic acid (OSA) and oligomers at very low pH so that stable solutions ready for use can be prepared which are bioavailable for man, plant and animal. Polymers of OSA are huge molecules (also called macromolecules) formed from hundred or thousands of units called monomers (OSA) whereas oligomers are molecules of intermediate size—much larger than monomers but less than macromolecules (Brinker C J et al, *Sol-Gel Science, The Physics and Chemistry of Sol-Gel processing*, Academic Press, Boston, p. 5) Choline plays also an important role in fat metabolism of humans and animals and is part of all kind of living cells in the form of a phosphatidyl choline, an important phospholipid of our cell membrane. Humans cynthesize choline from glycine, but this synthesis seems not to be enough for good health conditions all over the years. It is also present as acetylcholine, an important neurotransmitter. It is known as a vitamin B4. Moreover choline is an osmolyte and precursor of another important osmolyte, betaine. It is used as a food supplement in conditions as alcoholism, Alzheimer desease, angina pectoris, arteriosclerosis, asthma, cirrhosis of the liver, cystinuria, depression, diabetes, eczema, fatty liver, hair and nail problems, hepatitis, high cholesterol, hypertension, kidney liver damage, MS, etc. It is also related with the action of folate. Although most people take enough through their food (as lecithin), there are reports that most people lack choline. A low intake of folate could be the reason for the shortness of choline in the body. Recent preliminary studies in rats show that choline could be involved in the osteogenesis and bone remodeling (Gugulielmottic et al., *IADR 80 th General Session*, 2002) The daily intake of choline is estimated at 200-1000 mg/day. The national academy of sciences classified choline in 1998 as an essential nutrient (*Institute of Medicine, Food and Nutrition Board, Dietary reference Intake*, 1998, 390-422) after a study (Zeisel, 2000, *Nutrition*, 16, 669-671) showing that volunteers on a choline deficient diet were not able to produce enough choline. It was observed that choline deficiency causes histopathological changes in the cartilage similar to those found in manganese deficient chicks, i.e. poor developments of bones, joints and cartilage. The inter-relationship of choline, methionine and betaine and their differences was recently reviewed (Workel et al., 1998, *World Poultry*, 14, 1998). Choline alone is needed as essential constituent for phospholipids, normal maturation of cartilage matrix of bone, and prevention of perosis in broilers.

The role of silicon in plants, animals and humans is well documented. It is known that orthosilicic acid is the biological active molecule and also that silicon in food and drinking water has to be processed into orthosilicic acid to be absorbed and transported in the organism. Orthosilicic acid, a very weak acid, is not very stable at all pH lower than 9.5 and quickly precipitates or forms sols or gels which are not so bioavailable for the organisms. It is therefore very difficult to prepare highly concentrated (>0.5% silicon) solutions of orthosilicic acid and oligomers convenient as stock solution for the different organisms. In earlier patent applications (WO 95/21124) methods were described to prepare highly concentrated solutions, stable in time at different temperatures. These stock solutions are mostly very acid (pH<1) to prevent gel and sol formation. Their bioavailability is very high compared to other silicon compounds (silicates, clay, silica, horsetail, zeolites, . . . ), but those preparations are not stable after dilution.

Standard preparations were developed in order to obtain long-term solution of concentrated bioavailable choline—silicic aid (SA)—osmolyte solutions. From all osmolytes tested only formulations with choline in combination with betaine, inositol, ethanolamine, glycine, taurine and monomeric sugars as mannitol, sorbitol result in acid stable solutions. Because betaine could even be more involved in the role of preserving healthy bones, cartilage, hair, nails and all kinds of GAG systems, it is a preferred.

It was not known that these silicic acid dilutions could be used in plants (e.g. spraying on plant leaves) or in drinking water of a wide range of animals (e.g. pigs, poultry, horses). Therefore, specific solutions with the choline—silicic acid complex in water have been tested and prepared properly for specific use and compared for bioavailability and physiological effects. Hereafter are described the specific preparations for plants, animals and humans and the unexpected results using these preparations of the invention.

The benefits of calcium for plants and animals are well documented in the literature (Poovaiah et al., 1988, *Hortscience*, 23, 267-71; Dell et al., 1987, *Handbook of Nutritionally Essential Mineral Elements*, Marcel dekker, NY). It was not known that calcium is completely inert regarding OSA under pressure of choline and does not interfere with precipitation or gelification reaction of highly concentrated SA. In the literature it is known that the addition of salts accelerate gel formation, in particular calcium ions are known to be very effective (Heald et al., 1955, *J Appl Chem London*, 5, 425) on polymerization of silicon. After testing different combinations of $Ca^{2+}$ and OSA, it was surprisingly found that $Ca^{2+}$ does not interfere at pH-values<0.7 with highly concentrated SA. Dilutions showing pH values up to 7.5 are sufficiently stable at silicon concentration lower than 0.07%, which is convenient for use as plant nutrient solution, animal drinking water or spray for animal food. The introduction of calcium as $CaCO_3$ in the alkalinization step in our preparation is therefore appropriate. Other trace elements such as divalent ions as $Mn^{2+}$, $Sr^{2+}$, $Fe^{2+}$, $Cu^{2+}$, $Zn^{2+}$, $Mg^{2+}$ could be added at the same time in combination with $CaCO_3$ during or after the alkalinization step. The formation of chlorides and their solubility are the limiting factors. The addition of $Zn^{2+}$ is very interesting in animal applications because Zn is quickly eliminated from the body during the absorption of highly concentrated OSA so that an adequate Zn was the only element which was decreased in serum during OSA supplementation together with an inadequate Zn supplementation (low Zn diet). This observation is news and shows the importance of combining Zn with OSA during inadequate Zn supplementation. Interestingly, these results were not obtained in plants. The Zn concentration in plants was not affected after addition of concentrated OSA through sprays on the leaves. The SA-complex stock solution was diluted 1000 times and used as a spray for carrot plants during summertime (July and August). Carrots were analyzed for Si, Zn, Cu, Mg, Ca en Fe. There were no significant differences found for the metals except for Si which was doubled in concentration after spraying on the leaves once in a week. The addition of $CaCO_3$ during the alkalinization step in the preparation of SA-choline complex results in a stable solution (at low pH) and is highly bioavailable. Addition of other alkali (NaOH, KOH, etc.) to increase the pH up to 0.5, results in gelification after 1 week to 3 months. On the contrary, addition of CaCO3 gives stability for 2 years. We used also another compound for alkalinization instead of $CaCO_3$:betaine, an osmolyte. Combinations of calcium and the osmolytes and combinations of betaine and other osmolytes were also possible.

The present invention relates to biological preparations to a method for their preparation and to their use as nutrient and as medicament in the treatment of disorders and diseases.

It further relates to the use of a biological preparation as a plant nutrient and/or a fungal infection resistant agent, such as to decrease the concentration of pesticides and toxic compounds in the crop.

Formulations

All the formulations contain choline.

Formulation 1 with Calcium:

Choline chloride is dried under vacuum and is treated with dry hydrochloric acid. Silicon (IV) tetrachloride is added to the formed acid choline solution (ratio $SiCl_4$ versus choline chloride: 1 mol per 3 to 5 mol) at a temperature which is kept below 40° C.

For hydrolysis, water (ice/ice water) is added to the solution while cooling, wherein the temperature is held within the range of −10° C. to −30° C. A solution of 70-75% choline chloride in water is added to the hydrolysis solution in a ratio of 1 over 1. The resulting solution is alkalinized by the addition of anhydrous calcium carbonate in a concentration of 50 g $CaCO_3$ per liter.

Structure characterization using $^{29}Si$-NMR showed no signals between −30 and −70 ppm which is the spectral region for carbon bonded silicon (Si). The spectrum showed resonances around −72, −82, −92, −102 and −112 which are characteristic for $Q^0$, $Q^1$, $Q^2$, and $Q^4$ species respectively.

Formulation 2 with Calcium and Zinc:

A preparation as described in formulation 1 is prepared. $ZnCl_2$ is added after alkalinization at a final concentration of 100 mg Zn/ml.

Formulation 3 with Betaine:

Choline chloride is dried under vacuum and is treated with dry hydrochloric acid. Silicon (IV) tetrachloride is added to the formed acid choline solution (ratio $SiCl_4$ versus choline chloride: 1 mol per 3 to 5 mol) at a temperature which is kept below 40° C.

Solution A: For hydrolysis, water (ice/ice water) is added to the solution while cooling, wherein the temperature is held within the range of −10° C. to −30° C.

Solution B: A betaine solution is prepared in aqua destillata by adding to 1 liter of a.d. 1 to 1.5 kg of betaine.

1.8 liters of an aqueous 70-75% choline chloride solution is added to 2 liters of solution A. The resulting solution is alkalinized by the addition 0.2 liter of solution B.

Formulation 4 with Calcium and Betaine:

Choline chloride is dried under vacuum and is treated with dry hydrochloric acid. Silicon (IV) tetrachloride is added to the formed acid choline solution (ration $SiCl_4$ versus choline chloride: 1 mol per 3 to 5 mol) at a temperature which is kept below 40° C.

Solution A: For hydrolysis, water (ice/ice water) is added to the solution while cooling, wherein the temperature is held within the range of −10° C. to −30° C.

Solution B: A betaine solution is prepared in aqua destillata by adding to 1 liter of a.d. 1 to 1.5 kg of betaine.

1.8 liters of an aqueous 70-75% choline chloride solution is added to 2 liters of solution A.

The resulting solution is alkalinized by the addition of both 0.1 liter of solution B and anhydrous calcium carbonate (25 g $CaCO_3$ per liter).

Formulation 5 with Calcium and Taurine (100 mg/ml):

A preparation as described in formulation 1 is prepared. Taurine is added after alkalinization at a final concentration of 100 mg taurine per mililiter.

Formulation 6 with Betaine and Sorbitol (300 mg/ml):

Choline chloride is dried under vacuum and is treated with dry hydrochloric acid. Silicon (IV) tetrachloride is added to the formed acid choline solution (ratio $SiCl_4$ versus choline chloride: 1 mol per 3 to 5 mol) at a temperature which is kept below 40° C.

For hydrolysis, water (ice/ice water) is added to the solution while cooling, wherein the temperature is held within the range of −10° C. to −30° C. A betaine solution is prepared in aqua destillata by adding to 1 liter of a.d. 1 to 1.5 kg of betaine.

Solution A: For hydrolysis, water (ice/ice water) is added to the solution while cooling, wherein the temperature is held withi the range of −10° C. to −30° C.

Solution B: A betaine solution is prepared in aqua destillata by adding to 1 liter of a.d. 1 to 1.5 kg of betaine.

1.8 liters of an aqueous 70-75% choline chloride solution is added to 2 liters of colution A.

The resulting solution is alkalinized by the addition 0.2 liter of solution B. Sorbitol is added after alkalinization at a final concentration of 300 mg sorbitol per mililiter.

All preparations may also be combined with other divalent ions.

EXAMPLES

Example 1

Increased Water Retention in Plants

A betaine-choline-SA preparation (0.9% Si) was diluted one over 500 and sprayed weekly on lettuce crops. Fields with crops of the same origin and which were kept in the same culture conditions, were at the same time sprayed with a control (water) and a herbal silica extrct (*Equisetum arvense*). Several productin parameters of the harvested crops were investigated to document production quality, such as head firmness, marketable field, total fresh weight and loss of weight (table 1). Treatment with betaine-choline-SA resulted in the highest fresh weight and marketable field. The quality of the harvested crops was also higher after betaine-choline-SA treatment since both the loss of weight was lower during conservation and the head firmness was increased compared to either control or herbal silica treatments. These results indicate that the application of betaine-choline-SA increases the water retention of the plant.

TABLE 1

Effect of betaine-choline-SA on the production of lettuce.

| | Control | | Betaine-choline-SA | | Herbal silica | |
|---|---|---|---|---|---|---|
| | mean | rank (1) | Mean | rank (1) | mean | rank (1) |
| Head formation: (1-9)* | 7 | 1 | 7 | 1 | 6.375 | 3 |
| Head firmness: (1-9)* | 5.375 | 2 | 5.5 | 1 | 4.75 | 3 |
| Cut quality: | 56.73 | 3 | 59.93 | 1 | 58.22 | 2 |
| Marketable field kg/m²: | 2.27 | 2 | 2.58 | 1 | 2.21 | 3 |
| Left on field kg/m²: | 2.34 | 2 | 2.19 | 3 | 2.37 | 1 |
| Total fresh kg/m²: | 4.61 | 2 | 4.77 | 1 | 4.59 | 3 |
| Loss of weight after 5 days: | | | | | | |
| in cold store (4° C.): | 4.4 | 2 | 3.48 | 1 | 5.35 | 3 |
| at room temperature: | 22.79 | 3 | 21.28 | 1 | 22.19 | 2 |

TABLE 1-continued

Effect of betaine-choline-SA on the production of lettuce.

|  | Control | | Betaine-choline-SA | | Herbal silica | |
| --- | --- | --- | --- | --- | --- | --- |
|  | mean | rank (1) | Mean | rank (1) | mean | rank (1) |
| Loss of weight after 7 days: | | | | | | |
| in cold store (4° C.): | 7.55 | 2 | 5.38 | 1 | 8.18 | 3 |
| at room temperature: | 28.57 | 3 | 25.84 | 1 | 26.69 | 2 |
| Sum of ranks | | 24 | | 15 | | 26 |

(1) Rank: 1 = best treatment, 2 = second best treatment, 3 = worst treatment

Example 2

Increased bone density in chicks supplemented with betaine-choline-SA. Broiler chicks on a normal diet (1.4 mg Si/g) were supplemented with betaine-choline-SA (B-ch-SA) to investigate the effect of silicon on the serum calcium concentration and bone mineral content (BMC) density (BMD) in the femur.

A group of 42,500 chicks was administered B-ch-SA (13.5 mg Si/100 kg bodyweight/2 days) in their drinking water for 6 weeks which increased the total dietary Si intake with less than 0.5%. A control group of 42,600 chicks of the same age was started in parallel with identical feeding but without B-ch-SA supplementation. Samples of 30 randomly chosen chicks were taken in each group at the age of six weeks to analyse the serum calcium concentration and femora. Femoral BMC and BMD were analyzed by Dual Energy X-ray Absorptiometry. Scans were recorded for both total femur and five regions of interest in the femur. Differences between means were evaluated with a one-tailed Student t-test.

The serum Ca concentration was significantly higher ($p<0.05$) in supplemented chicks (74.85±13.82 mg/ml, n=60) compared to controls (69.47±15.99 mg/ml, n=60).

The BMC was significantly higher for supplemented chicks compared to the controls in all the scanned areas of the femur. Total BMC was also significantly higher (+8.4%, p=0.016) for supplemented chicks compared to controls.

The BMD was significantly higher at the midshaft (+4.25%, p=0.0209), the distal metaphysis (+4.88%, p=0.0102), and the hip region (+5.6%, p=0.014) for supplemented chicks compared to controls.

Increasing the total dietery intake of broiler chicks with less than 0.5% in the form of B-ch-SA resulted in a significant higher serum calcium concentration and higher bone mass and density in cortical and trabecular bone of the femur.

Example 3

Reduced White Mold Infection in Carrots

A common fungal infection in carrots is white mold infection (*Eryphe Heraclei*) of the leaves visualized as white spots. Fungicides are commonly used but have the disadvantage to be absorbed by the crops resulting in toxic or allergic reactions with the consumer.

A dilution of betaine-choline-SA was sprayed weekly on 3 different varieties of carrots (Nerac, Tyne, Napa) starting 3 months after sowing. Fields with crops of the same origin and kept at the same culture conditions were sprayed with fungicides. Both crops treated with betaine-ch-SA wnd with fungicides showed remarkable less white spots on the leaves already one week after the treatment was started compared to the untreated control crops. This difference in affected leaves was observed until harvesting of the crop (see table 2).

TABLE 2

Yields of crops after betaine-ch-SA application

| Crops | Yield Kg/are | White mold infection score (1) |
| --- | --- | --- |
| Untreated | 654 | 2 |
| betaine-ch-SA | 751 | 6, 5 |
| Fungicides | 775 | 7 |

(1) Score infection: 1 = severe infected, 9 = not infected

The production was found to be significantly higher after betaine-ch-SA treatment compared to untreated crops and comparable to crops which were treated with dungicides.

Example 4

Translocation of Silicon in Sweet Pepper

Sweet pepper was grown in a nutrient solution (hydraculture). Betaine-choline-SA was diluted 1 over 500 in the nutrient solution. Other plants of the same origin and kept at the same culture conditions, were not supplemented. The silicon concentration in leaves and roots was measured by atomic absorption spectrometry after 6 weeks supplementation. The silicon concentration in leaves was more than tenfold higher in leaves of plants supplemented with betaine-choline-SA compared to unsupplemented controls. These experiments clearly indicate that silicon from betaine-choline-SA is translocated from the root to the leaf.

Example 5

Reducing the Levels of Toxic Compounds in Plants

Pecticides are commonly used in the cultivation of crops to prevent or to treat fungal infections. However, the use of prophylactic agents has to be kept minimal due to their toxic nature for man, animals and the environment. Upper limits of residues are strictly regulated for the harvested crops and need to be as low as possible to guarantee the quality of the crop. Application of a calcium-choline-SA (see formulation I) dilution was found to:

i) make the crop more resistant against fungal infection which permits the use of lower dosages of fungicides.

ii) decrease the concentration of residues in the harvested crops.

a) Lettuce a calcium-choline-SA separation was added to the pesticide solution in a concentration of 3 ml/10 L. Control plants were treated only with pesticides (see table A). Three days after seedings were planted, foliar treatment was started and repeated 4 times. The period between treatments was each time 4 days. The crop was harvested three weeks after the last treatment and the concentration of residues (iprodione, dithiocarbamates) were analysed.

TABLE A

| | Pesticide treatments | |
|---|---|---|
| Foliar treatment | Pesticide (dose) | |
| 1st treatment | 80% thiram (30 g/L) | |
| 2nd | 48% mancozeb, 10% metalaxyl (25 g/L) | |
| 3rd | 50% iprodione (15 g/10 L) | |
| 4th | 80% thiram (40 g/L) 50% primicarb (5 g/10 L ) | |
| 5th | 200 g/L cyanamid (15 ml/10 L) | |

The concentration of residues was significantly lower when crops were treated with calcium-choline-SA preparation: a decrease of more than 64% and 30% was found for dithiocarbamates and iprodione respectively (see tabe B). None of the crops were infected with funghi.

TABLE B

| Residues of pesticides in lettuce treated with a calcium-choline-SA preparation. | | |
|---|---|---|
| | Dithiocarbamates (mg/kg) | Iprodione (mg/kg) |
| Control: pesticides | 14.6 | 2.45 |
| Pesticides + calcium-choline-SA preparation | 5.15 | 1.7 |

The silicon concentration was 45% higher in lettuce which was treated with calcium-choline-SA preparation (102 μg Si/g dry weight).

B) Potatoes

The incidence of *Phytophthora* infection was evaluated when combining a calcium-choline-SA preparation with a low dose of the commonly used fungicide Shirlan (fluazinam, 500 g/L). The minimal recommended dose of Shirlan is 0.4 liter per hectare to prevent *Phythophthora* infection of the crop. The crop remained healthly without a trace of *Phytophthora* infection when the fungicide dose was reduced with 50% and combined with 0.5 L calcium-choline-SA preparation per hectare, whereas untreated plots of plants were severely infected.

It is clear from the above examples that the new choline-SA preparations with in particular Ca and an osmolyte such as betaine, show very high bioavailability for plants and animals. These preparations may be used as nutrient and medicament for plant fortification and protection against different negative conditions (dry conditions, stress conditions from infections with microorganisms and insects). The preparations can be used for animals under a normal (silicon rich) diet. This means that these preparations (complex of choline-SA-osmolyte) are indeed active. They can therefore be used with good results for certain physiological conditions.

The invention claimed is:

1. A biological solution that is acidic and dilutable comprising:
bioavailable silicon in the form of orthosilicic acid and silicic acid at a silicon concentration of 0.9% or less;
a primary osmolyte choline; and
$CaCO_3$;
wherein the solution is stable for 2 years.

2. A biological solution that is acidic and dilutable comprising:
bioavailable silicon in the form of orthosilicic acid and silicic acid at a silicon concentration of 0.9% or less;
a primary osmolyte choline; and
betaine;
wherein the solution is stable for 2 years.

3. A diluted solution prepared by the method comprising:
(a) providing a biological solution that is acidic and dilutable comprising:
(i) bioavailable silicon in the form of orthosilicic acid and silicic acid at a silicon concentration of 0.9% or less;
(ii) a primary osmolyte choline; and
(iii) a weak alkalinizing agent without free hydroxyl groups selected from $CaCO_3$ and betaine; and
(b) diluting the biological solution to produce the diluted solution.

4. The diluted solution according to claim 3, wherein the diluted solution comprises the bioavailable silicon at a concentration of 0.07% or less.

5. A biological solution that is acidic and dilutable comprising:
bioavailable silicon in the form of orthosilicic acid and silicic acid at a silicon concentration of 0.9% or less;
a primary osmolyte choline; and
a weak alkalinizing agent without free hydroxyl groups selected from $CaCO_3$ and betaine;
wherein the solution is stable for 2 years and is prepared by the method comprising:
(a) hydrolyzing a silicon comprising choline solution thereby forming a choline stabilized orthosilic acid and oligomers solution;
(b) adding a concentrated choline solution to the choline stabilized orthosilic acid and oligomers solution; and
(c) alkalinizing the diluted choline stabilized orthosilicic acid and oligomers solution by adding a weak alkalinizing agent without free hydroxyl groups.

6. The biological solution of claim 5, further comprising a secondary osmolyte selected from the group of betaine, glycine, taurine, carnitine, inositol, ethanolamine, and their phosphates; mono sugars and combinations thereof.

7. The biological solution of claim 5, further comprising a divalent trace element.

8. The biological solution of claim 7, wherein the divalent trace element is $Ca^{2+}$, $Mn^{2+}$, $Sr^{2+}$, $Fe^{2+}$, $Cu^{2+}$, $Zn^{2+}$, or $Mg^{2+}$.

9. The biological solution of claim 7, wherein the divalent trace element is $Zn^{2+}$.

10. A stable dilution of the biological solution of claim 5.

* * * * *